United States Patent [19]
Sharp et al.

[11] Patent Number: 5,911,580
[45] Date of Patent: Jun. 15, 1999

[54] METHOD FOR PREPARING DENTAL MODELS

[75] Inventors: Michael C. Sharp, Centerport; Michael Barrett, Babylon; Nelson J. Gendusa, Manhasset, all of N.Y.

[73] Assignee: Parkell Products, Inc., Farmingdale, N.Y.

[21] Appl. No.: 08/791,656

[22] Filed: Jan. 30, 1997

[51] Int. Cl.$^6$ .............................. A61C 11/00; A61C 9/00
[52] U.S. Cl. ............................................ 433/213; 433/214
[58] Field of Search ................................ 433/37, 48, 213, 433/214

[56] References Cited

U.S. PATENT DOCUMENTS

| | | |
|---|---|---|
| 4,007,153 | 2/1977 | Smith . |
| 4,060,421 | 11/1977 | Yoshikawa et al. . |
| 4,273,902 | 6/1981 | Tomioka et al. . |
| 4,468,202 | 8/1984 | Cohen . |
| 4,543,372 | 9/1985 | Watanabe et al. . |
| 4,826,893 | 5/1989 | Yamazaki et al. . |
| 4,877,854 | 10/1989 | Hattori et al. . |
| 4,891,400 | 1/1990 | Schwabe et al. . |
| 4,970,245 | 11/1990 | Futami et al. . |
| 5,064,891 | 11/1991 | Fujiki et al. . |
| 5,081,164 | 1/1992 | Lai . |
| 5,387,105 | 2/1995 | Dougherty et al. . |
| 5,569,691 | 10/1996 | Guggenberger et al. . |

OTHER PUBLICATIONS

EOS "Extra Oral System For Chairside Inlays: Instructions for Use," Vivadent (date unknown).
Dr. B.–Jörg Heinenberg, "Die Neue Konzeption Eines Inlays," *Dental Magazin* (Feb. 1989).
EOS: Ästhetik für Anspruchsvolle, Vivadent Dental GmbH, Postfach 11 52, 7090 Ellwagen, Germany (date unknown).
EOS "The New Light–Curing Composite System for Immediate Chairside Indirect inlays and Veneers," Vivadent USA (date unknown).
"Silicones," *Concise Encyclopedia of Polymer Science and Engineering*, pp. 1048–1059 John Wiley & Sons, Inc., New York (1990).

*Primary Examiner*—Nicholas D. Lucchesi
*Attorney, Agent, or Firm*—Hoffmann & Baron, LLP

[57] ABSTRACT

A method of making solid die dental models is provided, comprising preparing an impression of a dental structure and fabricating a dental model using said impression by depositing therein a flowable modeling material which self-sets under ambient conditions to a substantially solid elastomeric state. The flowable modeling material preferably has an initial viscosity of less than about 30,000 cps, and preferably sets to a substantially solid state in less than about an hour to provide a solid elastomeric state having a durometer hardness of at least about 60. The resulting dental model can be employed for construction of accurate and precise composite dental restorations.

20 Claims, No Drawings

METHOD FOR PREPARING DENTAL MODELS

BACKGROUND OF THE INVENTION

The invention relates to methods of making dental models. In particular, the invention relates to methods of making solid dies suitable for preparing composite dental restorations.

In reconstructive dentistry, the construction of dental prosthetics, e.g., inlays, veneers, etc., benefits from being performed outside the mouth. Among other advantages, such an approach reduces patient discomfort, and facilitates manipulation of the restoration during construction.

Previously, this process required several time-consuming steps, and usually required the patient to make several visits to the dentist. Usually on the first visit, an elastomeric impression was taken and a temporary restoration fitted in the prepared tooth. Typically, this elastomeric impression is sent to a commercial dental laboratory for fashioning dies and models (positive replications) from the impression (negative registration). These positive replications are commonly fabricated from dental stones and/or epoxy materials. The commercial laboratory then constructs the dentist-prescribed restoration on the positive replication, and provides the completed restoration to the dentist. These are referred to as "indirect restorations."

On the next visit, the temporary restoration is removed, and the dentist then tries the laboratory fabricated restoration in the patient's prepared tooth to determine form, fit, and suitability of the restoration. If necessary, minor adjustments are made to the restoration, which is then permanently placed in the patient. If minor adjustments by the dentist cannot satisfactorily resolve fit and form problems, the restoration, along with the dies and models are returned to the commercial laboratory for re-make and re-trial, requiring installation of still another temporary restoration. Eventually the restoration is delivered to the patient. Typically, while the laboratory fabrication of dies models and restorations is ongoing, the temporary restoration causes patient inconvenience and discomfort and heightens tooth sensitivity. It would be beneficial to the patient to be able to take an impression, make the requisite dies and models, and fabricate and install a restoration all in a single visit, preferably in a minimum of time.

With respect to building indirect restorations, the ability to isolate the tooth or teeth to be restored by using an extra-oral model of the teeth makes the building process simpler and decreases patient discomfort. For example, ready access to the inlay site is gained and moisture problems are eliminated. Further, fabrication of an indirect restoration permits the dentist or a competent auxiliary technician to more precisely fashion a correct anatomical form for the restoration.

Moreover, modem composite inlay materials are light-curable. Curing such materials is easier outside the mouth. However a common option exercised with indirect resin composite restoratives is additional curing by heat application to the restoration. This is done by placing the light-cured restoration, with or without its attendant die, into a suitable thermostatically-controlled oven for a prescribed period (usually about 10 minutes) at a predetermined temperature (usually about 250° F.). This process effectively "post-cures" the resin composite, thereby improving the composite's physical properties.

Furthermore, a failing of currently available light-cured dental composite resins is the inherent tendency to shrink during polymerization. This shrinkage is invariably toward the source of polymerization initiation, typically a light source when resin composites are placed directly into a prepared tooth. This can result in marginal-gap formation with resultant tendencies for microleakage that can cause tooth sensitivity and potential for dental caries. With indirect, extra-oral polymerization, however, shrinkage occurs on the die/model, so the potential for marginal gapping is minimized.

Therefore, indirect methods permit the manufacture of higher quality restorations, leading to restorations which last longer, again improving patient satisfaction. Success, however, depends on the ability to make accurate and precise models of the teeth to be restored, with a minimum of cost in time and materials.

One type of dental model manufacturing method is described in a brochure from Vivadent USA. This method required use of a heavy viscosity condensation silicone putty as an impression material, and a vinyl siloxane as a modeling material. The modeling material apparently was also highly viscous, since it is described as requiring kneading or spatulating prior to use, presumably to mix the reactive components. Such inferior flow characteristics of the modeling material would also make it difficult to ensure that the impression was completely filled. It is believed that the modeling material was excessively flexible when set, making building of accurate restorations relatively difficult to accomplish. In addition, the use of siloxane impression and modeling materials required use of some additional material to prevent bonding of the materials. In any case, this procedure and the requisite materials proved cumbersome to use, and the system is no longer offered for sale to dentists.

In view of the above considerations, it is clear that existing methods and compositions for making dental models have defects which render them impractical or inconvenient for use. Typically, the compositions require too much handling, and the methods require numerous and complex procedures, thereby preventing completion of the restoration in a single visit, and requiring patients to return on subsequent visits. Conventional modeling materials have also been hard to handle, and suffer from excessive viscosity, rendering accurate modeling difficult.

Accordingly, it is one of the purposes of this invention to overcome the above limitations in the art of making models suitable for preparing dental restorations, by providing a method which is both simple and fast in execution. The method of the invention eliminates complex and time-consuming steps previously required to make dental models, enabling the practitioner to prepare a model, build a restoration, and implant the restoration into the patient in a single visit. A further purpose and advantage of the invention is to avoid the need to send an impression to an external, commercial laboratory for restoration manufacture. The method of the invention enables the dentist or an in-office auxiliary to quickly and easily create dies and models upon which high-quality and durable restorations can be fabricated, while eliminating the need for tooth temporization typically required during conventional indirect restoration fabrication methods, thus avoiding potential problems associated with such temporization procedures.

SUMMARY OF THE INVENTION

It has now been discovered that these and other objectives can be achieved by the present invention, which provides a method of making a dental model, comprising the steps of:

preparing an impression of a dental structure; and fabricating a dental model using the impression by depositing therein a flowable modeling material which self-sets under ambient conditions to a substantially solid elastomeric state having a durometer hardness of at least about 60.

The flowable modeling material preferably has an initial viscosity of less than about 30,000 cps. More preferably, the flowable modeling material has an initial viscosity of less than about 15,000 cps.

Moreover, the flowable modeling material preferably self-sets to a solid state in less than about 1 hour, more preferably self-setting to a solid state in less than about 15 minutes.

The method can further comprise the step of depositing into substantial co-extensive contact with the flowable modeling material a base material which self-sets to a substantially solid state under ambient conditions. The base material can be deposited prior to completion of setting of the flowable modeling material. Alternatively, the base material can be deposited after substantial completion of setting of the flowable modeling material.

The preparation of the impression can accomplished using a hydrocolloid impression material, preferably an alginate. However, the preparation of the impression can also be accomplished using an impression material selected from the group consisting of vinyl silicones and condensation silicones.

The flowable modeling material is preferably a vinyl silicone. Also, the base material is preferably a vinyl silicone. The flowable modeling material and the base material can be of different colors.

The method can further comprise coating the impression with a releasing agent to facilitate removal of the dental model from the impression.

It is preferred that the dental structure comprises a prepared tooth having a surface prepared for implantation of a composite restoration, and, therefore, the dental model will preferably comprise a replicate tooth corresponding to the prepared tooth. In this case, the method according can further comprise a step of preparing a composite restoration using the replicate tooth. Thus, the preparing step can comprise:

i) depositing a curable composite material onto the replicate tooth; and ii) curing the curable composite material in situ in the replicate tooth to provide a dental restoration suitable for implantation in the prepared tooth.

The method can also further comprise providing an adhesive or mechanical binder for promoting binding of the flowable modeling material with the base material.

The invention also includes a method of making a dental restoration, comprising:

a) preparing an impression of a dental structure comprising a tooth prepared for implantation of a composite restoration, using an impression material which self-sets to a substantially solid state under ambient conditions;

b) depositing into the impression a flowable modeling material which self-sets under ambient conditions to a substantially solid elastomeric state having a durometer hardness of at least about 60;

c) depositing into substantial co-extensive contact with the flowable modeling material a deformable base material which self-sets to a substantially solid state under ambient conditions;

d) setting the flowable modeling material and the deformable base material to provide a unitary dental model comprising a replicate tooth corresponding to the prepared tooth;

e) removing the dental model from the impression;

f) preparing a dental restoration by depositing a curable composite material onto the replicate tooth; and g) curing the curable composite material in situ in the replicate tooth creating the dental restoration suitable for implantation in the prepared tooth.

As a result of the invention, the manufacture of dental dies and models is readily accomplished within a dentist's office, and shipment of an elastomeric impression to a commercial dental laboratory is eliminated. Thus, the use of dies and dental models is simplified and made substantially faster, yielding models suitable for developing dental prosthetics in a single patient visit. These and other advantages of the present invention will be appreciated from the detailed description and examples which are set forth herein. The detailed description and examples enhance the understanding of the invention, but are not intended to limit the scope of the invention.

DETAILED DESCRIPTION OF THE PREFERRED EMBODIMENTS

The present invention is directed to a method of making dental dies and models, especially those which are suitable for use in preparing dental prosthetics, e.g., composite dental restorations, indirect composite inlays, chairside denture repairs, fast resin veneers or temporaries, and the like.

As used herein the term "dental model" refers to 3-dimensional, full-scale models of any or all of the dental structures, including the hard tissues, i.e., the teeth ("dentition") and/or the soft tissues, i.e., the gum ("gingival") structures. Typically, the practitioner requires accurate and precise models of the dentition, to permit fitting of restorative inlays, etc. Accordingly, the method can include taking an impression of the dentition and/or gingiva, to define an impression space which can then be filled with settable fluid materials, to provide a solid model of the desired structures. For example, according to the method of the invention a modeling material can be deposited to fill the entire dentition space, up to and including the gingival margins.

However, accurate and precise models of the gingival structures may be of special interest in cases where the restoration must account for prior tooth loss. In such cases, a modeling material may be used to fill not only the dentition space but also the gingival space defined with the impression. Alternatively, the artisan can employ the modeling material to fill and model the dentition space, and a base material to fill and model the gingival space. Such an approach is especially effective if the modeling material and the base material are color coded to more explicitly distinguish between the dental (hard) and gingival (soft) tissues.

The method comprises forming or casting a dental impression using a deformable impression material. Typically, the impression material is deposited into a tray, e.g., a quadrant tray, followed by impressing the tray onto the dental structures to be modeled. The impression material should be self-setting, and should be allowed to set at least partially prior to removal from the mouth, so that the impression does not deform upon removal. Following removal of the impression tray, the interior surface of the impression defines therein an impression space ("negative registration") which is complementary to or patterned on the 3-dimensional structure of the dental tissues. The impression space is nominally divisible into impression spaces corresponding to the dentition and the gingival structures. The dentition impression space and the gingival impression space are fully contiguous with one another, permitting preparation of a solid dental model representing or replicating any or all relevant dental structures.

Any conventional impression material can be used, provided that the material sets to a solid. The impression material should be self-setting, preferably setting within the space of a few minutes. Preferred impression materials include reversible and irreversible hydrocolloid-based compositions, such as alginate compositions, with irreversible materials generally being more preferred. Exemplary commercially available alginate materials include, for example, TRIPHASIX alginate available from Parkell and JELTRATE alginate available from Dentsply Int'l, Inc. Other impression materials are also commercially available, such as general impression materials, e.g., CINCH PLATNUM polyvinylsiloxane available from Parkell, as well as condensation silicones and polyethers, but these are typically substantially more expensive.

If an alginate impression material is employed, it is preferred to apply a surfactant ("wetting agent" or "debubbler") to the interior surface of the impression. Such materials inhibit the formation of bubbles when the modeling material is deposited into the impression, thereby ensuring a more accurate die. Surfactant materials are commercially available in spray form, e.g., from Aimore Int'l, Inc.

Alternatively, if a polyvinylsiloxane impression material is employed, it is desirable to coat the interior surface of the impression with a releasing agent to facilitate separation of the flowable modeling materials used to make the solid die. This is important if the impression material and the modeling material to be deposited into the impression space tend to adhere or bond to one another. Specifically, if the impression material and the modeling material are both vinyl silicone-based, a strong bond will generally form, requiring a releasing agent to disrupt any such bonding. Typically, the releasing agent is a friction-reducing agent such as an oil, but other materials which reduce the tendency of the impression material and the modeling materials to bond to or adhere to one another can be used. One particularly preferred class of releasing agents includes dry TEFLON/silicone sprays, such as the commercially available product SPL-88 by Handler Mfg. Co., Inc. Other materials such as sprayable vegetable oil materials, e.g., PAM spray, can be used. Other usable materials include mineral oils, petroleum jellies, and the like. Any functionally equivalent material can be used provided that it is not chemically incompatible with the impression material and the modeling material.

The modeling material in its unset state is "flowable," i.e., the material has an initial viscosity low enough to permit self-leveling prior to setting. Preferably, the initial viscosity of the modeling material is less than about 30,000 cps, more preferably less than about 15,000. Such low viscosity is beneficial in that uniform and consistent delivery of the material into the impression space is promoted, to ensure thorough occupation of the impression space without requiring additional physical manipulation, e.g., spatulation. The use of a flowable modeling material thereby permits accurate and precise rendition of even the smaller features of the dentition. Modeling materials which are too viscous, i.e., which require active deformation by being pressed or spatulated into the impression space, rather than simply flowing to occupy the impression space, are not acceptable.

Suitable modeling materials should self-set to a solid elastomeric state in less than about an hour under ambient conditions (e.g., room temperature, pressure, etc.), preferably within about 15 minutes, and more preferably within about 5 minutes. The modeling material should be compatible with both the impression material and the base material. Specifically, the modeling material should separate easily from the impression material (with or without use of a releasing agent), but preferably bonds strongly to the base material. It is further preferred that the modeling material have a higher hardness rating than the base material. This feature permits the resulting model to resist deformation during the process of constructing of indirect composite restorations, making the fit of the resulting restoration more accurate and more permanent. Suitable modeling materials typically have durometer (hardness) values of at least about 60, more preferably at least about 80. Durometer hardness is measurable using standardized techniques.

The flowable modeling material useful according to the invention is preferably elastomeric, e.g., a silicone. Various silicone compositions are known in the art, but many of these products are not acceptable for the method described herein inasmuch as they suffer from defects including, high initial viscosity, low durometer in the set state, long pot-life (long setting times), etc. As described herein, the modeling materials useful according to the invention have low initial viscosity, high durometer in the set state, and short pot-life (short setting times).

One especially preferred modeling material is a vinyl silicone sold under the name MACH-2 by Parkell Products, Inc., New York. This material is substantially non-adherent to hydrocolloid or alginate-type impression materials, permitting easy separation of the die following solidification. Moreover, the MACH-2 material bonds well to other vinyl siloxanes suitable for use as base materials. The MACH-2 material has a durometer of about 92–93, setting to a rigid state, yet permitting hardened restoratives, like light- and/or heat-cured resin composites, to release from undercuts in the die or model. This feature makes this material particularly resistant to deformation during the process of constructing indirect composite prosthetics, making the fit of the resulting prosthetic more accurate and more permanent.

In comparison to other commercially available materials, the MACH-2 product is advantageous in the method of the invention as it has an unusually low viscosity (being flowable as defined herein). Thus the use of MACH-2 permits the material to be easily extruded, and to flow readily into the impression space to model even minute details of the dental structures. Even so, the artisan appreciates that special care should be taken to avoid trapping bubbles in small cavities in the impression, especially in the prepared surfaces to be restored, since such bubbles will compromise the integrity of the resulting restoration. Surfactant materials may be coated onto the impression surface to eliminate bubbles prior to depositing the modeling material. Because the MACH-2 material sets quickly, typically in less than about 5 minutes, the practitioner may wish to start depositing the material in the site to be restored, i.e., the replicate tooth corresponding to the prepared tooth, filling the remainder of the impression afterward. Other functionally equivalent materials can be employed.

It is preferred that the impression material and the modeling materials be selected to inherently avoid bonding or adhering to one another. As noted, the MACH-2 material described herein does not effectively bond or adhere to alginate-type impression compositions, making it ideal for use according to the method of the invention. Accordingly, this pair of materials is highly preferred. Other substantially non-adherent pairs of materials may be selected on the basis of their physicochemical properties.

The base material can be any material which is initially substantially deformable, e.g., non-slumping or fluid, and which sets to a substantially solid, relatively undeformable state. Numerous materials meeting these criteria are known in the art, including plaster of Paris, dental stones, silicone polymers, etc.

In a preferred scenario, the base material is deposited directly onto the exposed surface of the modeling material while in the impression, in an amount sufficient to at least substantially cover the modeling material. Additional base material can be deposited into a base-former tray, and the base-former tray and the impression tray then placed into substantial co-extensive contact with one another prior to setting. This permits the base material in each tray to merge with the other to create a unitary base. The use of a base-former tray facilitates subsequent use of the solid die by providing a squared base to stabilize the model for building the restoration. This approach further facilitates reassembling separated dies (for convenient handling) in a precise and accurate relationship with adjacent segments of the dental model.

The base material should be deformable, but have a moderate viscosity to enable easy handling. Non-self-leveling and non-slumping materials are generally preferred, e.g, general impression materials of light to heavy body or bite registration materials can be used. Preferably, the base material should self-set quickly to a solid form, e.g., in about two minutes at about room (ambient) temperature. The set base material should be relatively hard, to provide stability when being worked to build the restoration.

As noted, numerous materials known in the art can be acceptable for use as base materials. Self-setting, elastomeric materials are preferred. Especially desirable base materials include fast-setting vinyl silicones materials such as BLU-MOUSSE and BLU-MOUSSE SUPER-FAST, available from Parkell. These materials bond well to vinyl silicone modeling materials, rendering them especially desirable in the present method.

The method of the invention can employ a flowable modeling material and a flowable base material which are color coded to differentiate or define the hard and soft tissues of the oral cavity. For example, the use of a modeling material which approximates the color or shade of teeth can provide an aesthetically appealing model. More important, however, a paler color is preferred because a paler surface will provide better reflectance (higher albedo) of the light delivered from a light-curing unit used to photo-polymerize resin composite restoratives.

In addition, the base material can be selected to contrast with the modeling material, to more effectively differentiate the modeled teeth to the observer. For example, the pale tan color of the MACH-2 modeling material described herein contrasts nicely with the blue color of the BLU-MOUSSE base material also described herein. Materials having other colors may be selected for particular purposes.

More important, the base material and the modeling material are preferably selected to adhere to or bond to one another, such that upon setting a unitary solid dental model is provided. It is possible, however, to provide a binder disposed between the modeling material and the base material, to promote binding of the two materials to one another and to impart to the model the desired unitary structure. But this approach is less desirable from the standpoint of convenience. For example, a binder such as a layer of adhesive or mechanical fasteners (e.g., pins, dowels, or screws) can be positioned between the modeling material and the base material. This can be accomplished after deposition of the modeling material but before the deposition of the base material. Alternatively, once the two materials have set to solids, the two pieces can be bound using such adhesives, fasteners, or other fictionally equivalent binders.

It is further desirable that the base material not adhere to the impression material, since the base material generally comes into contact with the impression when deposited onto the modeling material. Separation of the solid die from the impression can depend upon separability of the base material from the impression material. It is helpful if the base material is readily separable from the plastic base-former tray if such is used, since (optional) subsequent heat tempering of the restoration is generally performed at a temperature sufficient to melt the polymeric materials from which such trays are generally made.

The base material can be any material having the appropriate physical characteristics. Highly preferred base materials include vinyl polysiloxane materials, for example, BLU-MOUSSE and BLU-MOUSSE SUPER-FAST, both available from Parkell Products, Inc., New York. The BLU-MOUSSE materials are excellent for use in conjunction with the MACH-2 modeling material. Moreover, the BLU-MOUSSE materials have excellent hardness characteristics without any brittleness, having a durometer of about 85.

The following examples are provided to assist in a further understanding of the invention. The particular materials and conditions employed are intended to be further illustrative of the invention and are not limiting upon the reasonable scope thereof.

EXAMPLE 1

After preparing the tooth or teeth to be restored, a conventional alginate quadrant impression is taken to provide a negative registration of the dental structures of interest. (Double arch impression trays can also be employed to generate articulated impressions of upper and lower dental structures in one procedure. This is especially useful in the preparation of onlays and other restorations where the occlusal surface is substantially compromised.) A surfactant (debubbler) material may be employed, and the excess dumped. Then, using a standard impression gun for use with an auto-mix cartridge, MACH-2 silicone composition is extruded into the impression, first into the impression of the tooth/teeth being restored, then into the other teeth. A vibrator is not typically necessary to deposit the MACH-2 composition, due to its excellent flow characteristics, but a vibrator may be used if desired.

A cartridge gun is again used, to express a layer of BLU-MOUSSE SUPER-FAST onto the MACH-2 material, without waiting for the die material to set. A plastic base-former is filled with BLU-MOUSSE SUPER-FAST, and immediately seated onto the BLU-MOUSSE SUPER-FAST already resident in the impression. (The impression may be seated onto the base-former, but it is believed that the former procedure is more effective in avoiding sag of the impression and modeling material, and attendant deformation of the model.) After about two minutes, the solidified die is removed from the impression tray, and the base-former is removed from the die. Excess BLU-MOUSSE is trimmed with a razor blade or knife.

For preparing the restoration, the die is cut with a razor blade, to isolate the replicated tooth or teeth to be restored. The cut is made from the upper edge of the modeled teeth about two-thirds to three-fourths of the way toward the base. The base is then snapped, to provide an irregular surface permitting easy mating and reassembly of the pieces of the die if desired. If die trimming is required for easy access to the margins, a conventional blade is used.

A dental restoration is then built using the solid die by means of conventional techniques. Typically, a curable composite material is deposited into the replicated space corresponding to the prepared tooth, preferably using incremental build-up to ensure thorough polymerization. No prelubrication of the die is necessary, although a lubricant can be used if desired. The composite material is cured on the die, e.g., photo-polymerized using actinic light. The MACH-2 material is colored to approximate the color of the teeth and provides an excellent reflective surface to promote internal polymerization during the light curing process. Optionally, the cured composite is tempered by heating in a conventional toaster oven for about 10 minutes at about 250° F. The cured composite is then removed from the die (separating easily from the MACH-2 silicone), fit intraorally, and cemented into place. The skilled artisan will recognize the advantages inherent in the exemplary method described above, and will naturally adopt aspects of the method into his or her own practices in the construction of composite dental restorations.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the appended claims.

What is claimed is:

1. A method of making a dental model, comprising the steps of:

preparing an impression of a dental structure; and fabricating a dental model using said impression by depositing therein a flowable modeling material which self-sets under ambient conditions to a substantially solid elastomeric state having a durometer hardness of at least about 60.

2. A method according to claim 1, wherein said flowable modeling material has an initial viscosity of less than about 30,000 cps.

3. A method according to claim 2, wherein said flowable modeling material has an initial viscosity of less than about 15,000 cps.

4. A method according to claim 1, wherein said flowable modeling material self-sets to a solid state in less than about 1 hour.

5. A method according to claim 4, wherein said flowable modeling material self-sets to a solid state in less than about 15 minutes.

6. A method according to claim 1, wherein said method further comprises the step of depositing into substantial co-extensive contact with said flowable modeling material a base material which self-sets to a substantially solid state under ambient conditions.

7. A method according to claim 6, wherein said base material is deposited prior to completion of setting of said flowable modeling material.

8. A method according to claim 6, wherein said base material is deposited after substantial completion of setting of said flowable modeling material.

9. A method according to claim 1, wherein said preparing of said impression is accomplished using a hydrocolloid impression material.

10. A method according to claim 9, wherein said hydrocolloid impression material is an alginate.

11. A method according to claim 1, wherein said preparing of said impression is accomplished using an impression material selected from the group consisting of vinyl silicones and condensation silicones.

12. A method according to claim 1, wherein said flowable modeling material is a vinyl silicone.

13. A method according to claim 1, wherein said base material is a vinyl silicone.

14. A method according to claim 1, wherein said flowable modeling material and said base material are of different colors.

15. A method according to claim 1, further comprising coating said impression with a releasing agent to facilitate removal of said dental model from said impression.

16. A method according to claim 1, wherein said dental structure comprises a prepared tooth having a surface prepared for implantation of a composite restoration, and said dental model comprises a replicate tooth corresponding to said prepared tooth.

17. A method according to claim 16, further comprising a step of preparing a composite restoration using said replicate tooth.

18. A method according to claim 17, wherein said preparing step comprises:

i) depositing a curable composite material onto said replicate tooth; and ii) curing said curable composite material in situ in said replicate tooth to provide a dental restoration suitable for implantation in the prepared tooth.

19. A method according to claim 1, further comprising providing an adhesive or mechanical binder for promoting binding of said flowable modeling material with said base material.

20. A method of making a dental restoration, comprising:

a) preparing an impression of a dental structure comprising a tooth prepared for implantation of a composite restoration, using an impression material which self-sets to a substantially solid state under ambient conditions;

b) depositing into the impression a flowable modeling material which self-sets under ambient conditions to a substantially solid elastomeric state having a durometer hardness of at least about 60;

c) depositing into substantial co-extensive contact with said flowable modeling material a deformable base material which self-sets to a substantially solid state under ambient conditions;

d) setting said flowable modeling material and said deformable base material to provide a unitary dental model comprising a replicate tooth corresponding to said prepared tooth;

e) removing said dental model from said impression;

f) preparing a dental restoration by depositing a curable composite material onto said replicate tooth; and g) curing said curable composite material in situ in said replicate tooth creating the dental restoration suitable for implantation in the prepared tooth.

* * * * *